(12) United States Patent
Nadanami et al.

(10) Patent No.: US 6,337,009 B1
(45) Date of Patent: Jan. 8, 2002

(54) GAS SENSOR

(75) Inventors: Norihiko Nadanami, Komaki; Takafumi Oshima, Nagoya; Hiroki Fujita, Komaki; Ryuji Inoue, Tajimi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/523,198

(22) Filed: Mar. 10, 2000

(30) Foreign Application Priority Data

Mar. 12, 1999 (JP) .......................... 11-066994

(51) Int. Cl.$^7$ .............................. G01N 27/407
(52) U.S. Cl. ................. 205/775; 204/424; 204/426
(58) Field of Search ........................ 204/421–429; 205/775, 783.5–785

(56) References Cited

U.S. PATENT DOCUMENTS

| | | | | |
|---|---|---|---|---|
| 4,824,528 A | * | 4/1989 | Polak et al. | 204/425 |
| 4,859,307 A | * | 8/1989 | Nishizawa et al. | 204/426 |
| 5,215,643 A | * | 6/1993 | Kusanagi et al. | 204/426 |
| 5,302,274 A | * | 4/1994 | Tomantschger et al. | 204/426 |
| 5,387,329 A | * | 2/1995 | Foos et al. | 204/426 |
| 5,453,172 A | * | 9/1995 | Alberti et al. | 204/426 |
| 5,695,624 A | * | 12/1997 | Garzon et al. | 204/426 |
| 5,716,506 A | * | 2/1998 | Maclay et al. | 204/425 |
| 5,935,398 A | * | 8/1999 | Taniguchi et al. | 204/426 |
| 6,051,123 A | * | 4/2000 | Joshi et al. | 204/426 |
| 6,074,540 A | * | 6/2000 | Kroll et al. | 204/426 |
| 6,165,336 A | * | 12/2000 | Maki et al. | 204/426 |

FOREIGN PATENT DOCUMENTS

| | | |
|---|---|---|
| JP | 7-31153 | 4/1995 |
| JP | 8-327592 | 12/1996 |

* cited by examiner

Primary Examiner—T. Tung
(74) Attorney, Agent, or Firm—Sughrue Mion, PLLC

(57) ABSTRACT

A gas sensor comprising a proton-conductive layer 5 formed of a polymer electrolyte; first and second electrodes 3 and 4 disposed in contact with the proton-conductive layer 5 and having a function of dissociating hydrogen; a gas-diffusion-rate limiting layer 2 disposed between a measurement gas atmosphere and the first electrode 3 and adapted to diffuse the gas under measurement to the first electrode 3 in a diffusion-rate limited state; and a dense support 1 supporting these elements. Hydrogen gas having reached the first electrode 3 via the gas-diffusion-rate limiting layer 2 is dissociated into protons by virtue of the catalytic action of Pt contained in the electrode and the voltage applied to the first electrode 3, and the generated protons are pumped to the second electrode 4 via the proton-conductive layer 5 and are converted to hydrogen gas, which diffuses into the measurement gas atmosphere. When the applied voltage is sufficiently high, saturation current flows between the first and second electrodes 3 and 4, and the magnitude of the saturation current varies in proportion to the hydrogen gas concentration of the gas under measurement. A hydrogen gas sensor which operates at low temperature in a hydrogen-rich atmosphere, and which can accurately measure hydrogen gas concentration of a fuel gas of a fuel cell, is thereby provided.

17 Claims, 6 Drawing Sheets

GAS UNDER MEASUREMENT

GAS SENSOR

BACKGROUND OF THE INVENTION

1. Field of the Invention

The present invention relates to a gas sensor for use in measurement of the concentration of a hydrogen-containing component gas, and more particularly, to a hydrogen gas sensor suitable for measuring the concentration of a component gas, especially hydrogen gas, contained in a fuel gas for fuel cells.

2. Description of the Related Art

In view of the issue of global-scale environmental deterioration, fuel cells, which are clean and efficient power sources, have recently become the subject of active studies. Among fuel cells, a polymer electrolyte fuel cell (PEFC) is expected to be suitable for vehicle use due to its advantages, including low operation temperature and high output density. In this case, a reformed gas obtained from methanol or the like is advantageously used as a fuel gas. Further, in order to improve efficiency and other performance parameters, a gas sensor capable of directly measuring a hydrogen gas concentration or the like of the reformed gas becomes necessary. Since such a gas sensor is used in measurements performed in a hydrogen-rich atmosphere, the operation temperature of the gas sensor must be low (about 100° C. or less).

Such a low-operation-temperature-type hydrogen gas sensor is proposed in Japanese Patent Publication (kokoku) No. 7-31153. In the low-operation-temperature-type hydrogen gas sensor, a working electrode, a counter electrode, and a reference electrode are disposed on an insulating substrate, and the three electrodes are integrally covered with a gas-permeable, proton-conductive film.

Separately, a hydrogen gas sensor which operates at high temperature is proposed in Japanese Patent Application Laid-Open (kokai) No. 8-327592. This hydrogen gas sensor has a structure such that a porous positive electrode layer, a proton-conductive ceramic thin film, and a porous negative electrode layer are successively stacked on a porous ceramic substrate, and operates properly in a state in which the sensor is heated to a high temperature by use of a heater. In this hydrogen gas sensor, the porous ceramic substrate functions as a gas-diffusion-rate limiting layer.

In the hydrogen gas sensor proposed in Japanese Patent Publication No. 7-31153, since a gas under measurement diffuses to the working electrode via the gas-permeable, proton-conductive film which integrally covers the working electrode, the counter electrode, and the reference electrode, diffusion of the gas to the reference electrode cannot be prevented. Even when the reference electrode is formed of a metallic material having a low reactivity with the gas under measurement, the influence of the gas diffusion cannot be eliminated.

In the gas sensor, when the gas permeability of the proton-conductive film is lowered in order to decrease the amount of gas diffused to the reference electrode, a new problem arises in that the amount of gas diffused to the working electrode decreases accordingly, resulting in degraded sensitivity. Further, in the gas sensor, the proton-conductive film must be made porous in order to secure some degree of gas permeability. However, in this case, the mechanical strength of the proton-conductive film is reduced.

The hydrogen gas sensor proposed in Japanese Patent Application Laid-Open No. 8-327592 operates properly only at high temperature, because the proton-conductive layer is ceramic. From the viewpoint of safety, use of this gas sensor in a hydrogen-rich atmosphere is problematic. In addition, in the hydrogen gas sensor, since the porous ceramic substrate functions as a gas-diffusion-rate limiting layer, the strength of the substrate is low. Further, the substrate must be formed to be relatively large, in order to enable formation of the electrodes, the proton-conductive layer, etc. on the substrate through stacking. In a hydrogen gas sensor, such as the gas sensor proposed in Patent Application Laid-Open No. 8-327592, in which the substrate functions as a gas-diffusion-rate limiting layer, the size of the gas-diffusion-rate limiting layer is large, so that breakage of the gas-diffusion-rate limiting layer affects measurement to a greater extent than in the case in which a gas-diffusion-rate limiting layer of small size is used.

SUMMARY OF THE INVENTION

It is therefore an object of the present invention to provide a gas sensor which operates at low temperature in a hydrogen-rich atmosphere, and more specifically a hydrogen gas sensor capable of accurately measuring hydrogen gas concentration of a fuel gas of a fuel cell.

A first gas sensor according to the present invention comprises: a proton-conductive layer formed of a polymer electrolyte; first and second electrodes provided in contact with the proton-conductive layer and having a function of dissociating hydrogen gas; a gas-diffusion-rate limiting layer disposed between the first electrode and an atmosphere of a gas under measurement and adapted to diffuse the gas under measurement toward the first electrode in a diffusion-rate limited state; and a support for supporting the proton-conductive layer, the first and second electrode, and the gas-diffusion-rate limiting layer.

When gas concentration is measured by use of the gas sensor, the gas sensor is controlled as follows. By applying a predetermined voltage between the first and second electrodes, a predetermined gas component such as hydrogen gas is dissociated into protons on the first electrode. The thus-produced protons are pumped from the first electrode to the second electrode via the proton-conductive layer. Saturation current which flows from the first electrode to the second electrode as a result of the pumping out is detected, and the concentration of the predetermined gas component is determined on the basis of the saturation current.

In the gas sensor, since the gas-diffusion-rate limiting layer is provided, diffusion of the gas under measurement to the first electrode can be freely controlled with ease, without the necessity of changing the shape of the proton-conductive layer. Therefore, the magnitude of the saturation current, which determines the sensor sensitivity, can be changed freely, so that various measurement ranges can be used selectively.

In the gas sensor, since the diffusion rate of the gas under measurement is limited by the gas-diffusion-rate limiting layer, when the predetermined gas component contained in the gas under measurement has a constant concentration, the magnitude of current flowing between the first and second electrodes becomes substantially constant even when the voltage applied between the first and second electrodes exceeds a predetermined level. When current of a constant magnitude flows irrespective of the magnitude of the applied voltage, the current is called saturation current, and the magnitude of the current is called the "saturation current value."

Further, in the gas sensor, since the sensing portion of the gas sensor is formed on a support formed of an electrically insulative ceramic, the size of the sensing portion can be easily reduced without impairing of the overall mechanical strength of the gas sensor.

A second gas sensor according to the present invention comprises a reference electrode in addition to the structural elements of the above-described first gas sensor. The reference electrode is provided in contact with the proton-conductive layer such that an electrical potential corresponding to a reference hydrogen gas concentration is produced.

When a gas concentration is measured by use of the gas sensor, the gas sensor is controlled as follows. Voltage is applied between the first and second electrodes such that a predetermined voltage is produced between the first electrode and the reference electrode across the proton-conductive layer. Consequently, a gas component to be measured, such as hydrogen gas, which is contained in the gas under measurement and whose diffusion rate is limited by the gas-diffusion-rate limiting layer, is dissociated into protons. The thus-produced protons are pumped from the first electrode to the second electrode via the proton-conductive layer. The concentration of the gas component under measurement is determined on the basis of current which flows as a result of the pumping.

In the gas sensor, the voltage applied between the first and second electrodes can be controlled variably such that a constant voltage is produced between the first electrode and the reference electrode. Therefore, an optimal voltage can be applied to the gas sensor for any concentration of the gas component under measurement, so that accurate measurement can be performed in a wide concentration range.

Further, as in the above-described first gas sensor, in the second gas sensor, diffusion of the gas under measurement is limited by the gas-diffusion-rate limiting layer. Therefore, diffusion of the gas under measurement to the first electrode can be controlled, without changing the shape of the proton-conductive layer. Further, diffusion of the gas under measurement to the reference electrode can be easily prevented. Moreover, in the second gas sensor, freedom of design similar to that in the case of the first gas sensor is possible in relation to the material of the proton-conductive layer and use of the support.

A preferred mode of the present invention will now be described.

In a gas sensor according to the preferred mode of the present invention, a proton-conductive layer is formed of one or more types of fluororesins, more preferably of "NAFION" (trademark, product of Dupont).

In the gas sensor according to a preferred mode of the present invention, the proton-conductive layer is a polymeric electrolytic proton-conductive layer which operates adequately at a relatively low temperature, for example, temperatures not greater than 150° C., preferably, at temperatures not greater than 130° C., more preferably, at around 80° C.; e.g., a proton-conductive layer formed of a fluororesin-based solid polymer electrolyte.

In the gas sensor according to the preferred mode of the present invention, ceramic powder used as a material for the gas-diffusion-rate limiting layer has an average grain size of 2 to 80 $\mu$m. Preferably, the gas-diffusion-rate limiting layer is formed of porous alumina.

In the gas sensor according to the preferred mode of the present invention, the first and second electrodes and the reference electrode are formed of a material having a catalytic function. Preferably, these electrodes are formed of a Pt electrode material containing Pt or a Pt alloy as a main component.

In the gas sensor according to the preferred mode of the present invention, the support is comparatively dense, and preferably has a relative density of 95% or more.

In the gas sensor according to the preferred mode of the present invention, the first electrode has a gas-diffusion-rate limiting function. This eliminates the necessity of providing a separate gas-diffusion-rate limiting layer, to thereby further simplify the structure of the gas sensor. In this case, the first electrode is preferably formed of Pt powder having an average grain size of 2 to 50 $\mu$m.

The gas sensor according the preferred mode of the present invention can be fabricated as follows. By means of screen printing, a layer of alumina paste, which is to become the gas-diffusion-rate limiting layer, and layers of Pt-containing paste, which are to become the first and second electrodes and the reference electrode, are formed at predetermined positions on an alumina formed sheet, which is to become a support. Subsequently, the formed sheet and the paste layers are integrally fired, and a proton-conductive polymer electrolyte film, which is to become the proton-conductive layer, is bonded to a predetermined position of the fired body by means of hot pressing. Alternatively, a solution of a proton-conductive polymer electrolyte is applied to a predetermined position of the fired body and dried. The first and second electrodes and the reference electrode may be formed by a sputtering method. The method of fabricating the gas sensor according to the present invention is not limited to the above-described method.

In the gas sensor according to the preferred mode of the present invention, the first and second electrodes are formed to sandwich the proton-conductive layer. Alternatively, the first and second electrodes are formed on a common plane. When the first and second electrodes are formed on a common plane, the number of steps for forming the electrodes can be reduced.

In the gas sensor according to the preferred mode of the present invention, the gas-diffusion-rate limiting layer is formed on the surface of the support or within the support. When the gas-diffusion-rate limiting layer is formed (embedded) within the support, the structure of the gas sensor is simplified further.

In the gas sensor according to the preferred mode of the present invention, the reference electrode is formed such that the reference electrode is in contact with the proton-conductive layer, more preferably, is covered by the proton-conductive layer so as not to be exposed to a gas under measurement.

Figure 1:
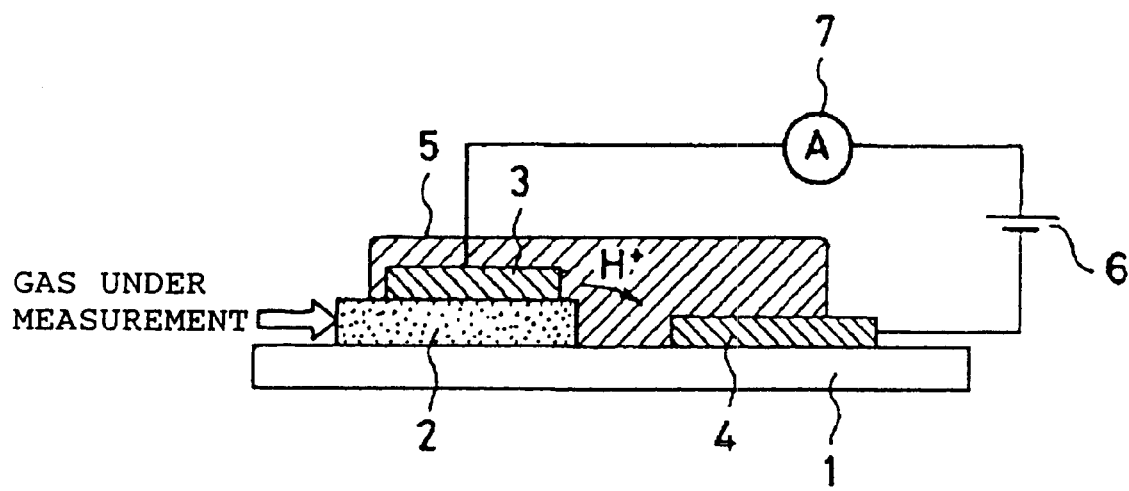
FIG. 1 is a sectional view of a gas sensor according to Embodiment 1 of the present invention.

Reference numerals are used to identify items in the drawings as follows:

1, 11, 21: support
2, 22: gas-diffusion-rate limiting layer
3, 23: first electrode
4, 14, 24: second electrode
5, 15, 25: proton-conductive layer
6, 16: power source
7, 17, 27: ammeter
13: first electrode (having an integral gas-diffusion-rate limiting function)
26: variable power source
28: reference electrode
29: voltmeter

DESCRIPTION OF THE PREFERRED EMBODIMENTS

The invention is next described by way of example and in reference to the drawings. However, the present invention should not be construed as being limited thereto.

Embodiment 1

FIG. 1 is a sectional view of a gas sensor according to Embodiment 1 of the present invention. As shown in FIG. 1, the gas sensor comprises a support 1 formed of comparatively dense ceramic, and a gas-diffusion-rate limiting layer 2 and a second electrode 4 are formed on the support 1 to be separated from each other in the layer plane. One end of the gas-diffusion-rate limiting layer 2 is exposed to an atmosphere containing a gas under measurement (hereinafter referred to as a "measurement gas atmosphere"). A first electrode 3 is formed on the gas-diffusion-rate limiting layer 2. Further, a proton-conductive layer 5 is formed on the support 1 such that the proton-conductive layer 5 covers the entirety of the first electrode 3 and a portion of the second electrode 4. A portion of the proton-conductive layer 5 enters the space between the gas-diffusion-rate limiting layer 2 and the second electrode 4 to thereby come in contact with the support 1.

The first and second electrodes 3 and 4 are formed of a porous Pt material through which gas can defuse and have a function of dissociating hydrogen gas. The gas-diffusion-rate limiting layer 2 is formed of porous alumina and has a gas-diffusion-rate limiting function. The proton-conductive layer 5 is formed of NAFION (trademark, product of Dupont, operation temperature: room temperature to 130° C.), which is one type of fluororesin, and has a proton-conducting function.

The gas sensor is fabricated as follows. By means of screen printing, a layer of alumina paste, which is to become the gas-diffusion-rate limiting layer 2, and layers of Pt-containing paste, which are to become the first and second electrodes 3 and 4, are formed at predetermined positions of an alumina formed sheet, which is to become the support 1. Subsequently, the formed sheet and the paste layers are integrally fired, and a film of NAFION, which is to become the proton-conductive layer 5, is bonded to a predetermined position of the fired body by means of hot pressing. Alternatively, a solution of NAFION is applied to a predetermined position of the fired body and dried. The first and second electrodes 3 and 4 may be formed by a sputtering method.

A series circuit comprising a power source 6 and an ammeter 7 is connected to the first and second electrodes 3 and 4 of the gas sensor via lead portions, so that a voltage is applied between the first and second electrodes 3 and 4. Current flowing between the first and second electrodes 3 and 4 can be measured by use of the ammeter 7.

Next, the measurement principle of the gas sensor will be described with reference to FIG. 1. In the following description, it is assumed that a gas component to be measured is hydrogen.

(1) Hydrogen gas having reached the first electrode 3 via the gas-diffusion-rate limiting layer 2 is dissociated into protons by means of the catalytic action of Pt contained in the first electrode 3 and the voltage applied to the first electrode 3.

(2) The generated protons are pumped to the second electrode 4 via the proton-conductive layer 5 and are converted to hydrogen gas, which diffuses into the measurement gas atmosphere.

(3) When the applied voltage described in (1) above is sufficiently high, a saturation current flows between the first and second electrodes 3 and 4. Since the magnitude of the saturation current varies in proportion to the hydrogen gas concentration of the gas under measurement, the hydrogen gas concentration can be obtained from the saturation current value.

The sensitivity of the gas sensor depends on the magnitude of the saturation current. That is, the sensitivity of the gas sensor depends on the degree of rate limiting of the gas-diffusion-rate limiting layer 2. Accordingly, the gas sensor can attain an optimal sensitivity through adjustment of the grain size and porosity of porous alumina that constitutes the gas-diffusion-rate limiting layer 2, irrespective of the shape of the proton-conductive layer 5.

Embodiment 2

In a gas sensor according to the present embodiment, a first electrode 13 (see FIG. 2) has a diffusion-rate limiting function, unlike the gas sensor according to Embodiment 1, in which the first electrode 3 and the gas-diffusion-rate limiting layer 2 are formed separately (see FIG. 1). In the gas sensor of the present embodiment, the first electrode 13 itself is formed to have a diffusion-rate limiting function by optimizing the grain size of Pt powder or the like which is used as an electrode material. This simplifies the sensor structure.

In order to avoid redundancy, the following description will describe only the difference between the sensor according to the present embodiment and the sensor according to Embodiment 1. For common features, the description of Embodiment 1 will be referred to as needed.

Figure 2:
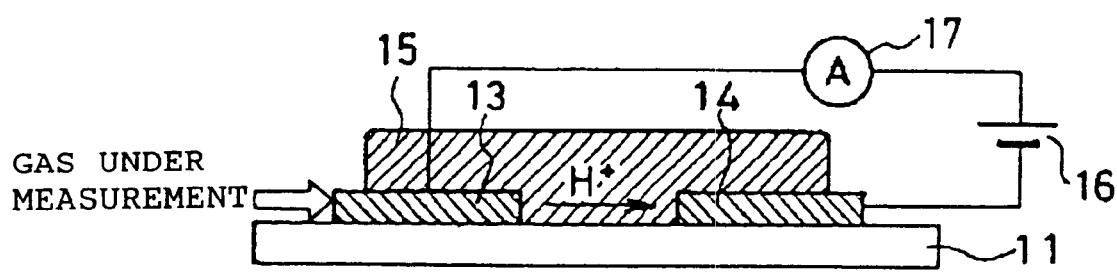
FIG. 2 is a sectional view of a gas sensor according to Embodiment 2 of the present invention.

FIG. 2 is a sectional view of a gas sensor according to Embodiment 2 of the present invention. As shown in FIG. 2, the gas sensor comprises a support 11 formed of comparatively dense ceramic, and a first electrode 13 and a second electrode 14 are formed on the support 11 to be separated from each other in the layer plane. One end of the first electrode 13 is exposed to a measurement gas atmosphere. Further, a proton-conductive layer 15 is formed on the support 11 such that the proton-conductive layer 15 covers a portion of the first electrode 13 and a portion of the second electrode 14. A portion of the proton-conductive layer 15 enters the space between the first electrode 13 and the second electrode 14 to thereby come in contact with the support 11.

The gas sensor is fabricated in a method basically identical with the method used for fabrication of the gas sensor according to Embodiment 1.

A series circuit comprising a power source 16 and an ammeter 17 is connected to the first and second electrodes 13 and 14 of the gas sensor via lead portions, so that a voltage is applied between the first and second electrodes 13 and 14. Current flowing between the first and second electrodes 13 and 14 can be measured using the ammeter 17.

The sensitivity of the gas sensor according to Embodiment 2 in measurement of hydrogen gas concentration was measured. More specifically, the saturation current flowing between the first and second electrodes was measured, while the hydrogen gas concentration of a gas under measurement was varied. The measurement conditions are shown below, and the measurement results are shown in FIG. 3.

Measurement Conditions:
First electrode: Pt electrode having a thickness of 20 $\mu$m;
Second electrode: Pt electrode having a thickness of 20 $\mu$m;
Support: alumina sheet having a thickness of 0.4 mm thickness and a relative density of 98%;
Composition of gas under measurement: $H_2$ (0–40%), $H_2O$ (10%), $N_2$ (bal.);
Temperature of gas under measurement: 80° C.;
Flow rate of gas under measurement: 4 L/min; and
Voltage applied between first and second electrodes: 1 V.

Figure 3:
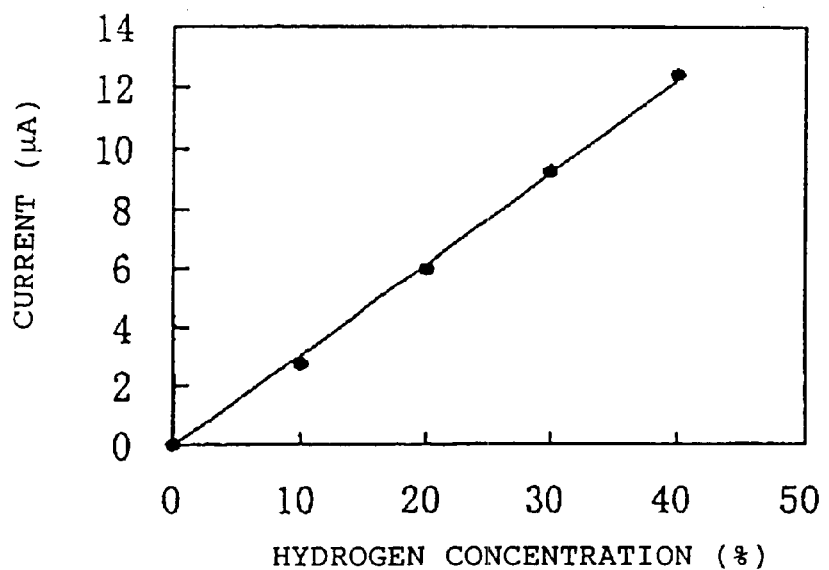
FIG. 3 is a graph showing results of a measurement performed using the gas sensor according to Embodiment 2 of the present invention.

As is understood from FIG. 3, the current varies in proportion to hydrogen gas concentration, which demonstrates that accurate measurement of hydrogen gas concentration can be performed in a wide range by use of the gas sensor. Further, the gas sensor was found to operate properly at temperatures not greater than 100° C.; more specifically, at temperatures not greater than 80° C.

Embodiment 3

Figure 4:
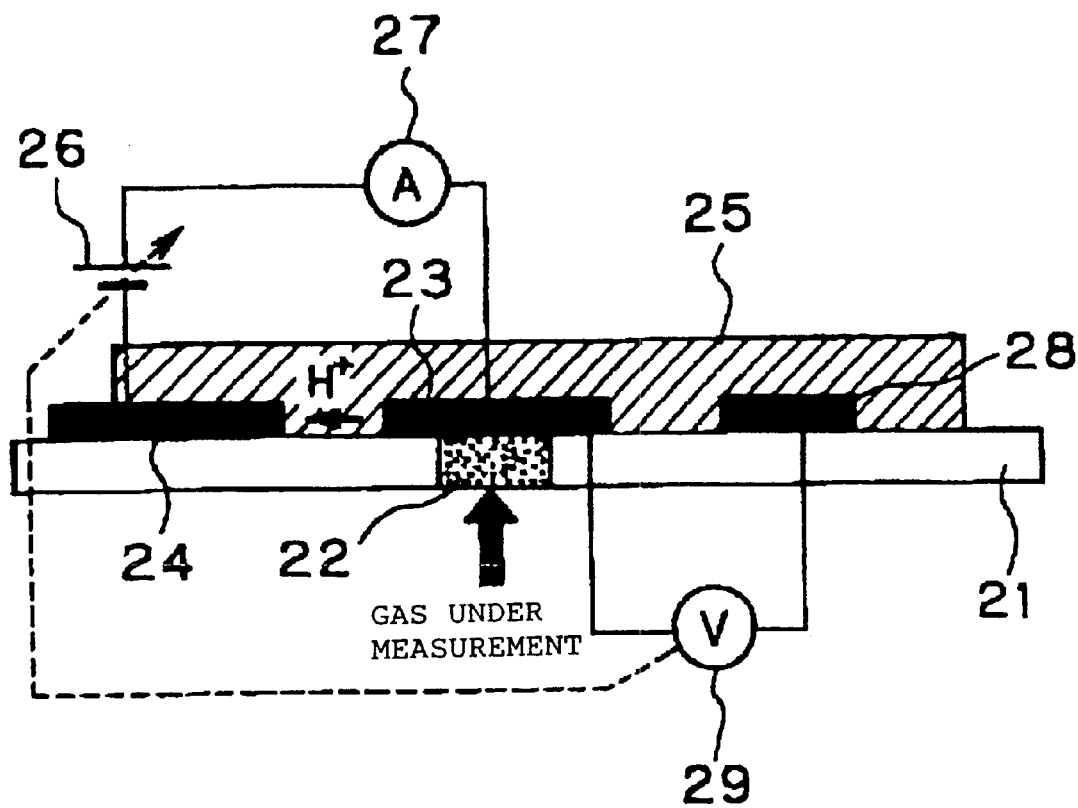
FIG. 4 is a sectional view of a gas sensor according to Embodiment 3 of the present invention.

FIG. 4 is a sectional view of a gas sensor according to Embodiment 3 of the present invention. As shown in FIG. 4, the gas sensor comprises a support 21 formed of comparatively dense ceramic, and a first electrode 23, a second electrode 24, and a reference electrode 28 are formed on the support 21 to be separated from one another in the layer plane. A gas-diffusion-rate limiting layer 22 is formed (embedded) within the support 21 to be located underneath the first electrode 23. Further, a proton-conductive layer 25 is formed on the support 21 such that the proton-conductive layer 25 covers the entirety of the first electrode 23, the entirety of the reference electrode 28, and a portion of the second electrode 24. Portions of the proton-conductive layer 25 enter the space between the first electrode 23 and the second electrode 24 and the space between the first electrode 23 and the reference electrode 28, respectively, to thereby come in contact with the support 21. Since the hydrogen gas concentration around the reference electrode 28 is stable, the reference electrode 28 generates a potential, or a reference hydrogen gas concentration potential, which serves as a reference for the potential of the first electrode 23.

The first and second electrodes 23 and 24 and the reference electrode 28 are formed of a porous Pt material through which gas can defuse sufficiently and have a function of dissociating hydrogen gas. The gas-diffusion-rate limiting layer 22 is formed of porous alumina and has a gas-diffusion-rate limiting function. The proton-conductive layer 25 is formed of NAFION and has a proton-conducting function.

The gas sensor is fabricated in a method basically identical with the method used for fabrication of the gas sensor according to Embodiment 1.

The electric circuit connected to the gas sensor has the following configuration. A series circuit comprising a variable power source 26 and an ammeter 27 is connected to the first and second electrodes 23 and 24 via lead portions, so that a voltage is applied between the first and second electrodes 23 and 24, and current flowing between the first and second electrodes 23 and 24 can be measured. A voltmeter 29 is connected between the first electrode 23 and the reference electrode 28 via lead potions. The voltage applied by means of the variable power source 26 is controlled in accordance with the voltage detected by means of the voltmeter 29. More specifically, the voltage applied between the first and second electrode 23 and 24 by means of the variable power source 26 is controlled such that the voltage between the first electrode 23 and the reference electrode 28 is maintained constant. In this state, the current flowing between the first and second electrodes 23 and 24 is measured by use of the ammeter 27.

Next, the measurement principle of the gas sensor will be described with reference to FIG. 4. In the following description, it is assumed that a gas component to be measured is hydrogen gas.

(1) When hydrogen gas reaches the first electrode 23 via the gas-diffusion-rate limiting layer 22, an electromotive force corresponding to the hydrogen gas concentration is generated between the first electrode 23 and the reference electrode 28 across the proton-conductive layer 25.

(2) A voltage is applied between the first and second electrodes 23 and 24 such that the hydrogen gas concentration on the first electrode 23 is maintained constant, i.e., the voltage between the first electrode 23 and the reference electrode 28 is maintained constant.

(3) As a result, the hydrogen gas is dissociated into protons on the first electrode 23, and the generated protons are pumped to the second electrode 24 via the proton-conductive layer 25. The protons are converted to hydrogen gas on the second electrode 24, and the thus-produced hydrogen gas diffuses into the measurement gas atmosphere.

(4) Since the magnitude of the saturation current flowing between the first and second electrodes 23 and 24 varies in proportion to the hydrogen gas concentration of the gas under measurement, the hydrogen gas concentration can be obtained from the saturation current.

Since the voltage applied between the first and second electrode 23 and 24 is controlled such that the hydrogen gas concentration on the first electrode 23 is maintained constant, high voltage can be applied when the hydrogen gas concentration of the gas under measurement is high, and low voltage can be applied when the hydrogen gas concentration of the gas under measurement is low. In other words, an optimal voltage can be applied between the first and second electrodes 23 and 24 in accordance with hydrogen gas concentration.

Further, in the gas sensor having the reference electrode 28, when the resistance between the first and second electrode 23 and 24 increases due to some reason, the applied voltage changes appropriately. Therefore, accurate measurement can be performed in a wide concentrate range for a prolonged period of time.

The saturation current characteristic of the gas sensor was measured. More specifically, the current flowing between the first and second electrodes 23 and 24 was measured, while the voltage applied between the first and second electrodes 23 and 24 was varied. The measurement conditions are shown below, and measurement results are shown in FIG. 5.

Measurement Conditions:
   First electrode: Pt electrode having a thickness of 20 μm;
   Second electrode: Pt electrode having a thickness of 20 μm;
   Reference electrode: Pt electrode having a thickness of 20 μm;
   Support: alumina sheet having a thickness of 0.4 mm and a relative density of 98%;
   Composition of gas under measurement: $H_2$ (0, 10, 20, 30, 40%), $H_2O$ (20%), $CO_2$ (15%), $N_2$ (bal.);
   Temperature of gas under measurement: 80° C.;
   Flow rate of gas under measurement: 4 L/min; and
   Voltage applied between first and second electrodes: 0–800 mV.

Figure 5:
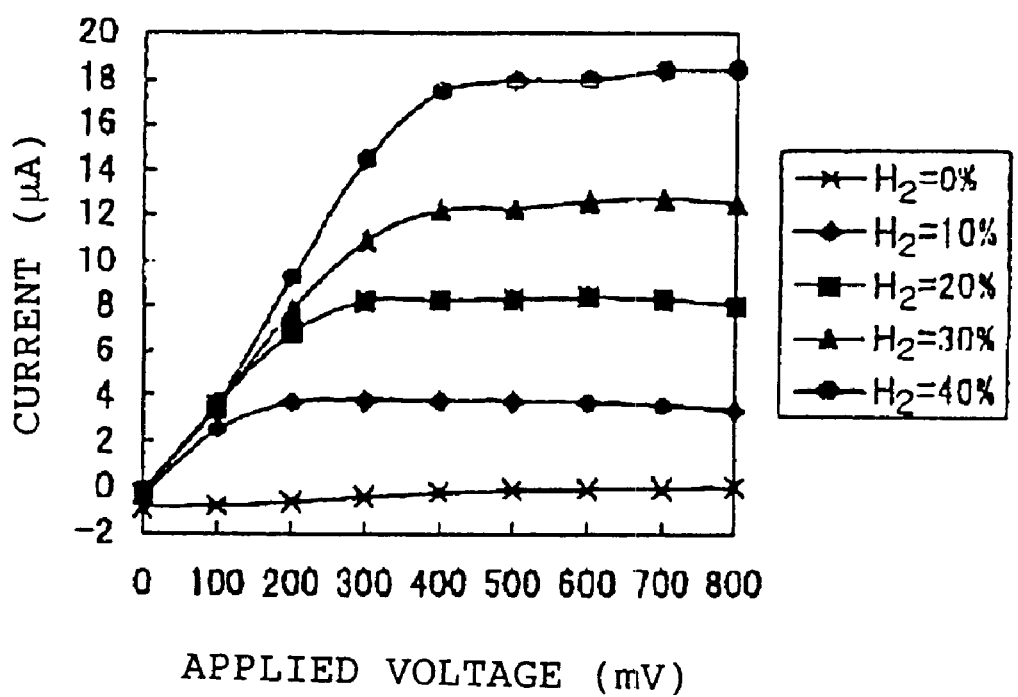
FIG. 5 is a graph showing results of a measurement performed using the gas sensor according to Embodiment 3 of the present invention.

As is understood from FIG. 5, for each hydrogen gas concentration, saturation current flows when the applied voltage exceeds 400 mV.

Subsequently, the sensitivity of the gas sensor in measurement of hydrogen gas concentration was measured. More specifically, the saturation current flowing between the first and second electrodes was measured, while the voltage applied between the first and second electrodes was controlled such that the voltage between the reference electrode and the first electrode was maintained at 600 mV, and the hydrogen gas concentration of a gas under measurement was varied. In addition, in order to further stabilize the hydrogen gas concentration in the vicinity of the reference electrode, a constant small current was caused to flow from the first electrode to the reference electrode such that the reference electrode served as a self-generation reference electrode. The measurement conditions are shown below; the relationship between hydrogen gas concentration and current is shown in FIG. 6; and the relationship between hydrogen gas concentration and voltage applied between the first and second electrodes is shown in FIG. 7.

Measurement Conditions:
   Composition of gas under measurement: $H_2$ (0, 10, 20, 30, 40%), $H_2O$ (20%), $CO_2$ (15%), $N_2$ (bal.);
   Temperature of gas under measurement: 80° C.;
   Flow rate of gas under measurement: 4 L/min;
   Target value of the voltage between the reference electrode and the first electrode: 600 mV; and
   Current for generation of self reference electrode flowing from the first electrode to the reference electrode: 1 μA.

Figure 6:
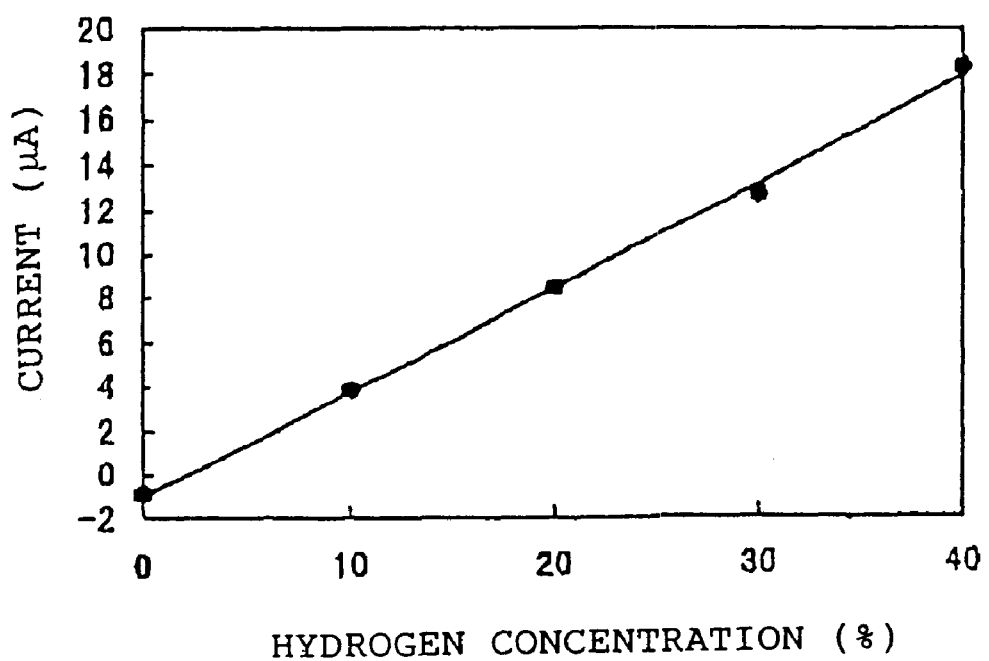
FIG. 6 is a graph showing results of another measurement performed using the gas sensor according to Embodiment 3 of the present invention.
Figure 7:
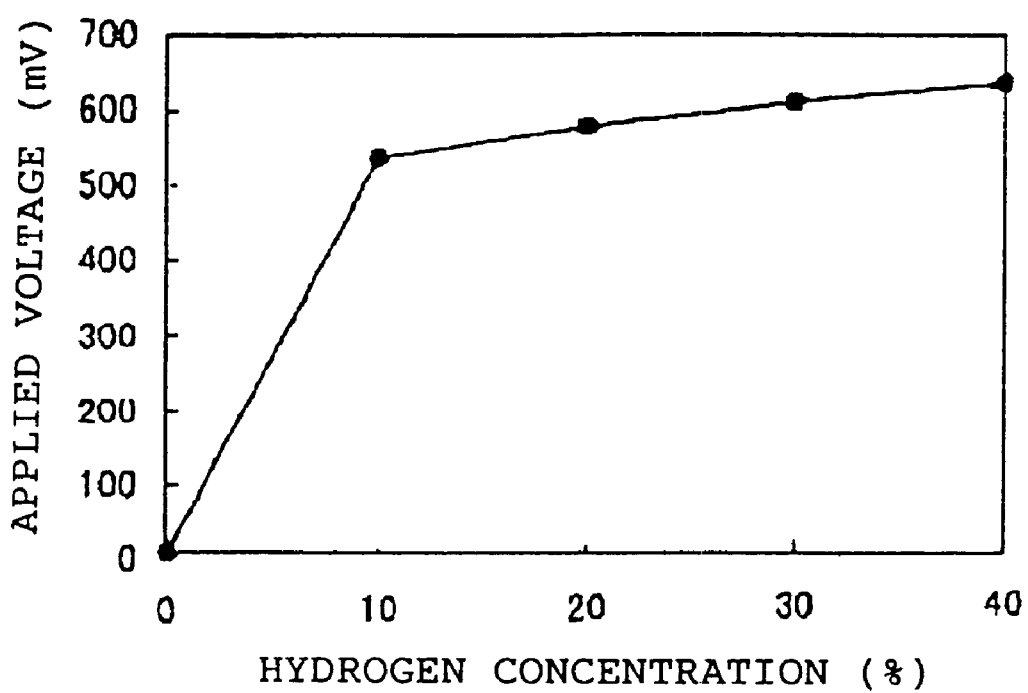
FIG. 7 is a graph showing results of another measurement performed using the gas sensor according to Embodiment 3 of the present invention.

As is understood from FIG. 6, the current varies in proportion to hydrogen gas concentration, which demonstrates that accurate measurement of hydrogen gas concentration can be performed in a wide range by use of the gas sensor. Further, as is understood from FIG. 7, an optimal voltage is applied between the first and second electrodes for each hydrogen gas concentration. That is, disposition of the reference electrode enables application to the gas sensor of an optimal voltage for varying hydrogen gas concentration to thereby enable accurate measurement of hydrogen gas concentration to be performed for a long period of time without causing deterioration of electrodes and the like. Moreover, the gas sensor was found to properly operate at temperatures not greater than 100° C.; more specifically, at temperatures not greater than 80° C.

The present invention provides a gas sensor capable of operating at low temperature in a hydrogen-rich atmosphere, and more specifically a hydrogen gas sensor capable of accurately and safely measuring a hydrogen gas concentration of a fuel gas of a fuel cell.

Having described specific preferred embodiments of the present invention, it is to be understood that the invention is not limited to those precise embodiments, and that various changes and modifications may be effected therein by one skilled in the art without departing from the scope of the invention as defined in the appended claims.

This application is based on Japanese Patent Application No. Hei. 11-66994 filed Mar. 12, 1999, the disclosure of which is incorporated herein by reference in its entirety.

What is claimed is:

1. A gas sensor comprising:
   a proton-conductive layer formed of a polymeric electrolyte;
   first and second electrodes provided in contact with the proton-conductive layer for dissociating hydrogen gas;
   a gas-diffusion-rate limiting portion for diffusing a gas under measurement from an atmosphere of the gas under measurement to the first electrode in a diffusion-rate limited state; and
   an electrically insulative support for supporting the proton-conductive layer and the first and second electrodes,
   wherein the gas-diffusion-rate limiting portion comprises a layer arranged between the support and the first electrode or is embedded within the support underneath the first electrode.

2. The gas sensor according to claim 1, wherein hydrogen contained in the gas under measurement introduced via the gas-diffusion-rate limiting portion is caused to undergo dissociation, decomposition or reaction by applying a voltage between the first and second electrodes; protons produced by said dissociation, decomposition or reaction are pumped from the first electrode to the second electrode via the proton-conductive layer to result in a current flow between said first and second electrodes; and the hydrogen concentration of the gas under measurement is determined based on said current flow.

3. The gas sensor according to claim 2, wherein said current flow is a saturation current.

4. The gas sensor according to claim 1, wherein the first electrode and the gas-diffusion-rate limiting portion are integrated.

5. The gas sensor according to claim 1, wherein the gas-diffusion-rate limiting portion is embedded within the support.

6. The gas sensor according to claim 1, wherein the proton-conductive layer is formed of a fluororesin.

7. The gas sensor according to claim 1, wherein the support is formed of a dense ceramic.

8. The gas sensor according to claim 1, further comprising:
   a reference electrode provided in contact with the proton-conductive layer for producing an electric potential corresponding to a reference hydrogen gas concentration, wherein said reference electrode is supported on said support.

9. The gas sensor according to claim 8, wherein a constant voltage is produced between the first electrode and the reference electrode when a voltage is applied between the first and second electrodes.

10. The gas sensor according to claim 8, wherein the reference electrode is formed on the surface of the support.

11. The gas sensor according to claim 1, wherein the gas-diffusion-rate limiting portion comprises a layer arranged between the support and the first electrode.

12. A gas sensor system comprising:
   a gas sensor comprising a proton-conductive layer formed of a polymeric electrolyte, first and second electrodes provided in contact with the proton-conductive layer for dissociating hydrogen gas, a gas-diffusion-rate limiting portion for diffusing a gas under measurement from an atmosphere of the gas under measurement to the first electrode in a diffusion-rate limited state, and an electrically insulative support for supporting the proton-conductive layer and the first and second electrodes;

a voltage source for applying a voltage between the first and second electrodes such that hydrogen contained in the gas under measurement introduced via the gas-diffusion-rate limiting portion is caused to undergo dissociation, decomposition or reaction; and a circuit for measuring current flow between said first and second electrodes, wherein the gas-diffusion-rate limiting portion comprises a layer arranged between the support and the first electrode or is embedded within the support underneath the first electrode.

13. The gas sensor system according to claim 12, wherein protons produced by said dissociation, decomposition or reaction are pumped from the first electrode to the second electrode via the proton-conductive layer to result in a current flow between said first and second electrodes; and the hydrogen concentration of the gas under measurement is determined based on said current flow.

14. A method of measuring the hydrogen concentration of a gas under measurement with a gas sensor comprising a proton-conductive layer formed of a polymeric electrolyte, first and second electrodes provided in contact with the proton-conductive layer for dissociating hydrogen gas, a gas-diffusion-rate limiting portion for diffusing the gas under measurement from an atmosphere of the gas under measurement to the first electrode in a diffusion-rate limited state, and an electrically insulative support for supporting the proton-conductive layer and the first and second electrodes, wherein the gas-diffusion-rate limiting portion comprises a layer arranged between the support and the first electrode or is embedded within the support underneath the first electrode, which method comprises applying a voltage between the first and second electrodes of the gas sensor such that hydrogen contained in the gas under measurement introduced via the gas-diffusion-rate limiting portion is caused to undergo dissociation, decomposition or reaction; and measuring current flow between said first and second electrodes.

15. The method according to claim 14, which comprises pumping protons produced by said dissociation, decomposition or reaction from the first electrode to the second electrode via the proton-conductive layer to result in a current flow between said first and second electrodes.

16. The method according to claim 15, wherein said current flow is a saturation current.

17. The method according to claim 14, wherein said gas sensor further comprises a reference electrode provided in contact with the proton-conductive layer for producing an electric potential corresponding to a reference hydrogen gas concentration, said reference electrode being supported on said support, and which comprises producing a constant voltage between the first electrode and the reference electrode when a voltage is applied between the first and second electrodes.

* * * * *